US006217943B1

(12) United States Patent
Hall et al.

(10) Patent No.: US 6,217,943 B1
(45) Date of Patent: Apr. 17, 2001

(54) AROMATIC CYANATE ESTER SILANE COUPLING AGENTS

(75) Inventors: Joyce B. Hall, North St. Paul; Fred B. McCormick, Maplewood; Kim M. Vogel, Lake Elmo, all of MN (US); Hiroyaki Yamaguchi, Tokyo (JP)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 09/286,061

(22) Filed: Apr. 5, 1999

Related U.S. Application Data

(62) Division of application No. 08/446,876, filed on Jun. 5, 1996, now Pat. No. 5,912,377.

(51) Int. Cl.$^7$ ....................................... B05D 3/00
(52) U.S. Cl. ..................... 427/387; 428/447; 556/415; 560/301
(58) Field of Search .................... 427/387; 428/447; 556/415; 560/301

(56) References Cited

U.S. PATENT DOCUMENTS

| 3,190,762 | 6/1965 | Carlson et al. ..................... 106/90 |
| 4,797,454 | 1/1989 | Ryang ................................ 525/476 |
| 4,845,257 | * 7/1989 | Naito et al. ..................... 556/415 X |
| 4,983,644 | * 1/1991 | Mukai et al. ......................... 522/14 |
| 5,143,785 | 9/1992 | Pujoi et al. ........................ 428/352 |
| 5,210,247 | * 5/1993 | Haberle et al. ................. 556/415 X |
| 5,214,176 | * 5/1993 | Soula et al. ..................... 556/415 X |
| 5,215,860 | 6/1993 | McCormick et al. ............... 430/270 |
| 5,260,398 | 11/1993 | Liao et al. .............................. 528/15 |
| 5,330,684 | 7/1994 | Emori et al. ......................... 252/512 |
| 6,005,047 | * 12/1999 | Shaffer et al. ...................... 524/590 |

FOREIGN PATENT DOCUMENTS

| 7-179839 | * 7/1995 | (JP) . |
| WO 93/17860 | 9/1993 | (WO) . |

OTHER PUBLICATIONS

"Silane Coupling Agents"(1982), published by Plenum (NY), pp. 1–28.
Fyfe et al., *Journal of Polymer Science: Part A; Polymer Chemistry*, vol. 32, 1994, pp. 2203–2221.
Patent Abstracts of Japan, vol. 17, no. 420 ( C–1093) [6049], 5 Aug. 1993 & JP,A,05 086214, abstract.
Patent Abstracts of Japan, vol. 16, no. 513 (E–1283) [5556], 22 Oct. 1992 & JP,A,04 192489, abstract.
Patent Abstracts of Japan, vol. 14, no. 287 (M–988) [4230], 21 Jun. 1990 & JP, A,02 089634, abstract.

* cited by examiner

*Primary Examiner*—Erma Cameron
(74) *Attorney, Agent, or Firm*—Philip Y. Dahl

(57) ABSTRACT

A composition of matter comprises an aromatic cyanate ester silane comprising at least one cyanate ester group and at least one hydrolyzable silyl group. In the presence of a cyanate ester resin the aromatic cyanate ester silane acts as a coupling agent to improve the adhesion of the cyanate ester to a substrate. The curable compositions are useful as reinforced composites, and as adhesive and coating compositions.

17 Claims, 2 Drawing Sheets

AROMATIC CYANATE ESTER SILANE COUPLING AGENTS

This is a division of application Ser. No. 08/446,876 filed Jun. 5, 1995 now U.S. Pat. No. 5,912,377.

FIELD OF THE INVENTION

This invention relates to novel aromatic cyanate ester silanes which contain aromatic cyanate ester groups and hydrolyzable silyl groups. Curable compositions comprising a cyanate ester resins and the aromatic cyanate ester silane as a coupling agent provide adhesives and protective coatings.

BACKGROUND OF THE INVENTION

Cyanate ester resins have utility in a variety of composite, adhesive, and coating applications, such as circuit board laminates, conductive adhesives, structural adhesives, protective coatings, aerospace structures, filled molded parts, structural composites, and semiconductor encapsulants, where adhesion between the cyanate ester resin and a surface is of critical importance.

Adhesion of polymers to substrates has long been a problem in adhesive and coating chemistry and in making of polymer composites. One solution has been the use of silane coupling agents as described, for example, by Plueddemann in the book "Silane Coupling Agents," published in 1982 by Plenum (New York), pp. 1–28. Typically, silane coupling agents have the structure $X-Y-SiZ_3$ where X is a functional group capable of interacting, or preferably, reacting, with the polymeric resin, Y is an organic linkage, and at least one Z is a reactive or hydrolyzable group capable of reacting with hydroxyl groups on the surface of the substrate. The X group bonds with the polymer network and the $SiZ_3$ group bonds to the substrate. This provides a chemical link (covalent bonds) from the polymer to the substrate through the organic group Y and thereby improves the adhesion of the polymer to the substrate. Numerous silane coupling agents have been developed for a variety of polymeric resins, but it is believed a silane coupling agent has never been developed specifically for cyanate ester resins.

Existing silane coupling agents have been used with cyanate ester resins. For example, U.S. Pat. Nos. 5,143,785 and 5,330,684 describe cyanate ester based conductive adhesives which may incorporate silane coupling agents where the X group, shown above, is mercapto, epoxy, acryloyl, or amino. A preferred coupling agent may be 3-glycidoxypropyltrimethoxysilane which was used exclusively in the examples of U.S. Pat. No. 5,143,785. Mercapto, hydroxy, and amino groups are known to react with cyanate esters but may produce undesirable side reactions and thermally or hydrolytically unstable bonds. Additionally, amino groups react too rapidly with cyanate esters to be of practical value and are catalysts for cyanate ester cure which leads to reduced shelf life for the adhesive. The '684 patent requires that an epoxy resin be present in conductive adhesive composition. Numerous patents, see U.S. Pat. No. 4,797,454, for example, have reported that epoxy groups couple with cyanate ester groups by the formation of oxazoline groups. However, recent research results reported by Fyfe and coworkers (Journal of Polymer Science: Part A: Polymer Chemistry, Vol. 32, 1994, pp. 2203–2221) show that the reaction of cyanate esters with epoxy compounds is very complex and does not produce oxazoline structures. These researchers report that the direct reaction of cyanate esters and epoxies provides oxazolidinone structures and that this is a minor reaction pathway. This type of complex and inefficient chemistry is undesirable for a coupling agent.

SUMMARY OF THE INVENTION

Briefly, a composition of matter comprises an aromatic cyanate ester silane comprising at least one aromatic cyanate ester and at least one hydrolyzable silyl groups. When present in admixture with a cyanate ester resin, the aromatic cyanate ester silane is a coupling agent for the resin.

In a further aspect, methods for preparing the composition of the present invention are described. The aromatic cyanate ester silane compounds are novel and are prepared from aromatic hydroxyl compounds which contain at least one olefinic double bond, which preferably is an aliphatic or cycloaliphatic carbon-to-carbon double bond, by a combination of hydrosilation and cyanation reactions.

In yet a further aspect, a method of coupling a cyanate ester resin to a substrate by means of the aromatic cyanate ester silane coupling agent of the invention is described.

In a still further aspect, an adhesive film which optionally can include conductive particles, and which includes the curable composition of matter of the present invention comprises a cyanate ester resin and an aromatic cyanate ester coupling agent as well as a thermoplastic polymer.

In this application:

"cyanate ester" means a derivative of cyanic acid (HOCN) in which the H is replaced by an organic group, preferably an aromatic group;

"silane" means a silicon containing compound having at least one single bond between the silicon atom and a carbon atom of an organic group; and "hydrolyzable silyl group" means a silicon atom and its substituents, whereby at least one and up to three of the substituents may be cleaved by water or alcohol to produce one to three OH groups attached to the silicon.

The novel coupling agents of the present invention provide a means by which cyanate ester resins can have improved adhesion to inorganic or organic surfaces. The resulting curable compositions can have utility in reinforced composites and in a variety of adhesive and coating applications, such as circuit board laminates, conductive adhesives, structural adhesives, structural composites, protective coatings, aerospace structures, filled molded articles, and semiconductor encapsulants. In these applications adhesion between the cyanate ester resin and an substrate is of critical importance.

It has now been discovered that silane coupling agents incorporating aromatic cyanate ester groups and hydrolyzable silyl groups can be prepared and that they improve the adhesion of cyanate ester resins to substrates.

DETAILED DESCRIPTION OF PREFERRED EMBODIMENTS OF THE INVENTION

Figure 1:
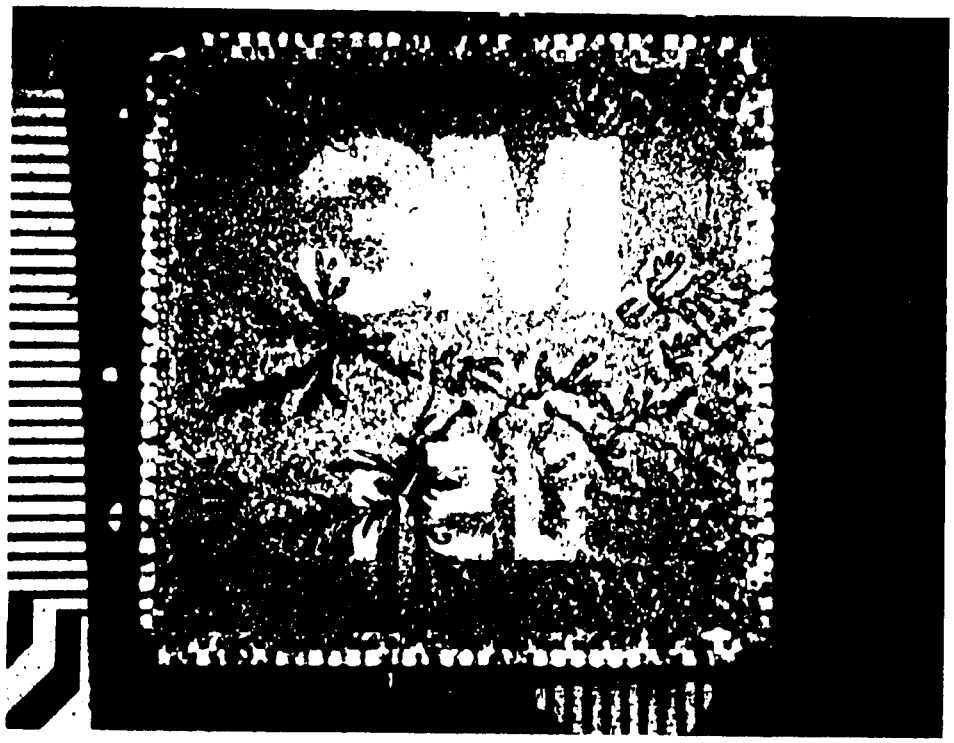
FIG. 1 is a micrograph (9.5× enlarged) showing a 3M test chip bonded, using a composition of the present invention, to an indium-tin oxide glass substrate.

The silane coupling agents of the present invention can be prepared from aromatic hydroxyl compounds which contain at least one olefinic double bond by two different methods.

Method A comprises first reacting an aromatic hydroxyl compound which contains at least one olefinic double bond with cyanogen halide and a base to give an aromatic cyanate ester compound which contains at least one olefinic double bond. The aromatic cyanate ester compound which contains at least one olefinic double bond can then be hydrosilated to give the aromatic cyanate ester silane coupling agents of the present invention.

Method B comprises first hydrosilating an aromatic hydroxyl compound which contains at least one olefinic double bond to give an aromatic hydroxyl compound which contains at least one silyl group. The aromatic hydroxyl compound which contains at least one silyl group can then be reacted with cyanogen halide and a base to give the aromatic cyanate ester silane coupling agent of the present invention.

The hydrosilation reaction is typically carried out in the presence of a suitable catalyst and may be carried out with or without solvent as described by Speier in "Advances in Organometallic Chemistry," Volume 17, Academic Press, Inc., pp. 407–447, 1979. The reaction is usually conducted from −40° C. to about 150° C., preferably from about −20° C. to about 120° C., more preferably from about 0° C. to about 80° C. Suitable catalysts for the hydrosilation reaction include, but are not limited to, chloroplatinic acid, bis(divinyltetramethyldisiloxane)platinum, tris(triphenylphosphine)rhodium chloride, platinum on carbon, and colloidal platinum metal. Bis(divinyltetramethyldisiloxane)platinum, chloroplatinic acid, and platinum on carbon are the preferred catalysts.

Silanes, which comprise at least one Si—H group, which can be used in the hydrosilation reaction to prepare the coupling agents of this invention, can have the general formula

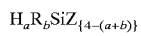

$H_a R_b SiZ_{\{4-(a+b)\}}$ where H is a hydride group directly bound to the silicon (Si) atom, a=1 to 3, preferably 1 or 2, most preferably 1, R is a nonfunctionalized alkyl or aromatic group, b=0 to 2, preferably 0 or 1, with the proviso that a+b is less than or equal to 3, and at least one Z is a hydrolyzable group capable of reacting with a hydroxyl group preferably on a substrate. It is understood that the hydrolyzable group can react directly with a hydroxyl group or its hydrolysis product can react with a hydroxyl group. The hydrolyzable groups are typically halogen or alkoxy groups, and —Cl, —OCH$_3$, or —OCH$_2$CH$_3$ are the preferred hydrolyzable groups. Illustrative examples of the silanes useful in the hydrosilation reaction leading to the coupling agents of this invention include, trichlorosilane, triethoxysilane, trimethoxysilane, dimethylchlorosilane, dimethylethoxysilane, ethyldichlorosilane, dichloromethylsilane, cyclohexyldichlorosilane, cyclopentyldichlorosilane, dichlorosilane, diisopropylchlorosilane, hexadecyldichlorosilane, hexyldichlorosilane, hexyldimethoxysilane, isobutyldiethoxy silane, methyldiethoxysilane, methyldimethoxysilane, and phenyldichlorosilane. Triethoxysilane, trimethoxysilane, and trichlorosilane are preferred silanes for the preparation of the coupling agents of this invention by hydrosilation reactions.

The aromatic hydroxyl compounds which comprise at least one olefinic double bond or at least one silyl group can be converted to a cyanate ester compound by reaction with preformed cyanogen halide or in situ formed cyanogen halide in the presence of a base as described, for example, by Martin and Bauer in Organic Syntheses, Volume 61, pp. 35–38, 1983. The reaction is conducted at a temperature between about −60° C. to about 60° C., preferably from about −10° C. to 10° C. for a time sufficient to complete the reaction, usually from about 0.1 to 10 hours, preferably from about 0.2 to about 5 hours, and more preferably from about 0.2 to 2 hours. The reaction is usually carried out in the presence of a suitable solvent such as, for example, toluene, methylene chloride, tetrahydrofuran, dichloroethane, acetonitrile, diethyl ether, glyme, and combinations thereof Methylene chloride is a preferred solvent. Tertiary amines are typically used as the base in the reaction, although other bases may be used. Triethyl amine is a preferred base. In a typical reaction, the aromatic hydroxyl compound and an excess of the cyanogen halide are dissolved in methylene chloride and cooled to the preferred temperature range. Triethyl amine is then slowly added, usually through an addition funnel in a dropwise manner, such that the temperature of the reaction solution does not exceed the preferred range. After further stirring, the reaction is quenched with water and the cyanate ester product is isolated by standard chemical techniques.

Suitable aromatic hydroxyl compounds which can be employed in this method to prepare silane coupling agents containing cyanate ester functional groups of the present invention include any compound containing at least one aromatic hydroxyl group per molecule and also at least one straight chain or branched aliphatic or cycloaliphatic carbon-to-carbon double bond per molecule. Such aromatic hydroxyl compounds include, but are not limited to, those represented by the general formula

HO—Ar—U wherein Ar can be a single aromatic ring, or it can be two or more fused aromatic rings or two or more aromatic rings connected by at least one of a) a carbon-carbon single bond, b) a hydrocarbyl group, c) an ether group, or d) a thioether group; Ar can comprise 5 to 30 carbon atoms and zero to five O, N, S, and P heteroatoms; HO can be one or more hydroxyl groups directly bound to one of the aromatic rings of Ar; and U can be at least one olefinically unsaturated straight chain or branched aliphatic or olefinically unsaturated cycloaliphatic group having 2 to 30 carbon atoms directly bound to one of the aromatic rings of Ar. The Ar group may further contain organic substitutents such as alkyl, alkoxy, halo, ester, sulfide, and ketone groups provided these groups do not interfere with the synthesis or use of the coupling agents of this invention. The U group may contain ether, thioether, ester, or ketone linkages or other organic substituents provided these linkages or organic substituents (which substituents can also include halo atoms) do not interfere with the synthesis or use of the coupling agents of this invention. Examples of Ar groups include benzene, naphthalene, 2,2-diphenylpropane, diphenyl ether, and biphenyl. Examples of U groups include vinyl, allyl, —O—CH═CH$_2$, —O—CH$_2$—CH═CH$_2$, cyclohexenyl, cyclopentenyl, and —CH$_2$—(CH$_2$)$_x$—CH═CH$_2$ where x can be an integer 1–5.

Illustrative examples of aromatic hydroxyl compounds containing aliphatic or cycloaliphatic carbon-to-carbon double bonds include 2-allylphenol, 4-allylphenol (also called 4-(2-propenyl)phenol), 4-propenylphenol, 4-hydroxystyrene, the monoallylether of bisphenol A, 4-allyl-2-methoxyphenol (also called eugenol), 2-propenylphenol, 2-methoxy-4-propenylphenol (also called isoeugenol), 2-ethoxy-5(1-propenyl)phenol, and 4-allyl-2,6-dimethoxyphenol.

Generally, for each equivalent of the aromatic hydroxyl compound containing olefinic unsaturation it is preferred to use excess amounts of the other reactants in preparing the aromatic cyanate ester silane coupling agents of the invention.

The ability to synthesize the coupling agents of this invention was surprising. The hydrosilation reaction requires transition metal catalysts, some of which are organometallic compounds, and it is well known, as described in U.S. Pat. No. 5,215,860, for example, that such materials are also catalysts for the cyclotrimerization of cyanate ester groups. Thus, the catalytic hydrosilation of olefinic double bonds in compounds which also contain cyanate ester groups could be expected to cause the cyclotrimerization of the cyanate ester groups. In such a case, the resulting triazine would not be effective as a coupling agent. The conversion of aromatic hydroxyl groups to cyanate ester groups by reaction with cyanogen halide typically requires aqueous conditions in the isolation of the product. Additionally, the reaction is often carried out in a two-phase system where one phase is aqueous as described in the Martin and Bauer reference cited previously. Thus, reaction of an aromatic hydroxyl compound which also contains hydrolyzable silane (SiZ as disclosed above) groups with cyanogen halide under typical conditions would be expected to result in the hydrolysis of the silane groups. This would provide a complex mixture of products which could not readily be separated or purified. Additionally, significant amounts of, for example, alcohol or hydrochloric acid could be produced in the hydrolysis reaction depending on the nature of the hydrolyzable silane groups. Alcohols and acids are known to react with cyanate ester groups and their presence could adversely affect the stability of the desired coupling agent product. Surprisingly, the methods of the present invention can provide the desired coupling agent isolatable as a pure compound despite undesirable side reactions.

Method A of the preparation of the coupling agents of this invention can follow the steps of a) providing an aromatic hydroxyl compound which contains at least one aliphatic or cycloaliphatic carbon-to-carbon double bond, b) reacting the aromatic hydroxyl compound with cyanogen halide and a base where a preferred reaction temperature between −10° C. and 10° C. is maintained, and c) reacting the resulting cyanate ester compound with a silane containing both Si—H bonds and hydrolyzable groups in the presence of a hydrosilation catalyst where a preferred reaction temperature below 100° C. is maintained. Hydrolyzable groups such as methoxy, ethoxy, or chloro are required so that the resulting aromatic cyanate ester silane will be a coupling agent.

Illustrative of a Reaction Scheme for Method A is as follows:

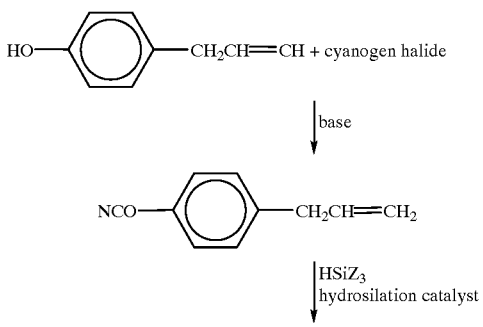

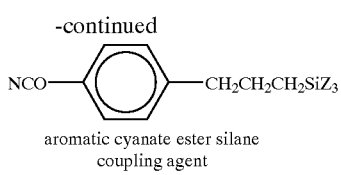

aromatic cyanate ester silane
coupling agent wherein Z is as defined above.

Method B of the preparation of the coupling agents of this invention can follow the steps of a) providing an aromatic hydroxyl compound which contains at least one aliphatic or cycloaliphatic carbon-to-carbon double bond, b) reacting the aromatic hydroxyl compound with a silane containing both Si—H bonds and hydrolyzable groups in the presence of a hydrosilation catalyst where a preferred reaction temperature below 100° C. is maintained, and c) reacting the resulting aromatic hydroxyl compound which contains at least one silyl group with cyanogen halide and a base where a preferred reaction temperature between −10° C. and 10° C. is maintained. Hydrolyzable groups on silicon, as noted above, are required so that the resulting aromatic cyanate ester silane will be a coupling agent.

Illustrative of a Reaction Scheme for Method B is as follows:

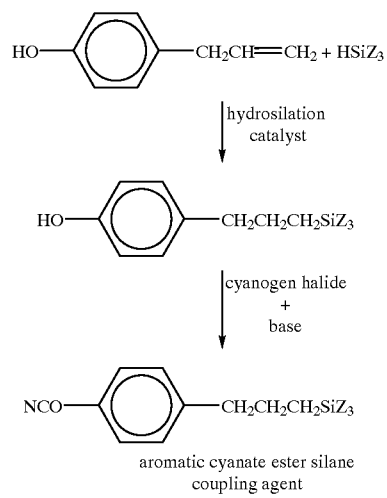

aromatic cyanate ester silane
coupling agent wherein Z is as defined above.

The coupling agents of this invention prepared by the above methods can have the general formula

where Ar is as described above, NCO is a cyanate group directly bound to an aromatic ring of Ar, c can be an integer 1 to 5, preferably 1 or 2, U' is an organic group resulting from the hydrosilation of the group U described above, a can be an integer 1 to 3, preferably 1 or 2, most preferably 1, R can be as described above, b can be 0 or 1 or 2, preferably 0 or 1, with the proviso that a+b is less than or equal to 3, and Z is as described above. Examples of U' groups resulting from the hydrosilation of the U groups described above include ethylene, propylene, —O—$CH_2$—$CH_2$—, —O—CH($CH_3$)—, —O—$CH_2$—$CH_2$—$CH_2$—, —O—$CH_2$—CH($CH_3$)—, cyclohexylene, cyclopentylene, —$CH_2$—$(CH_2)_x$—$CH_2$—$CH_2$— where x=1–5, and —$CH_2$—$(CH_2)_x$—CH($CH_3$)— where x can be 1–5.

Illustrative examples of the coupling agents of this invention include 3-(4-cyanatophenyl)propyltrimethoxysilane, 3-(2-cyanatophenyl)propyltrimethoxysilane, 3-(4-cyanatophenyl)propyltriethoxysilane, 3-(4-cyanatophenyl)propyltrichlorosilane, 3-(2-cyanatophenyl)propyltriethoxysilane, 3-(2-cyanatophenyl)propyltrichlorosilane, 3-(3-cyanatophenyl)propyltriethoxysilane, 3-(3-cyanatophenyl)propyltrichlorosilane, 3-(3-cyanatophenyl)propyltrimethoxysilane, 2-trimethoxysilyl-1-(4-cyanatophenyl)propane, 2-triethoxysilyl-1-(4-cyanatophenyl)propane, 2-trichlorosilyl-1-(4-cyanatophenyl)propane, 2-trimethoxysilyl-1-(2-cyanatophenyl)propane, 2-triethoxysilyl-1-(2-cyanatophenyl)propane, 2-trichlorosilyl-1-(2-cyanatophenyl)propane 2-triethoxysilyl-1-(3-cyanatophenyl)propane, 2-trichlorosilyl-1-(3-cyanatophenyl)propane, 2-trimethoxysilyl-1-(3-cyanatophenyl)propane, 1,1-trimethoxysilyl(4-cyanatophenyl)propane, 1,1-triethoxysilyl(4-cyanatophenyl)propane, 1,1-trichlorosilyl(4-cyanatophenyl)propane, 1,1-trimethoxysilyl(2-cyanatophenyl)propane, 1,1-triethoxysilyl(2-cyanatophenyl)propane, 1,1-trichlorosilyl(2-cyanatophenyl)propane, 1,1-triethoxysilyl(3-cyanatophenyl)propane, 1,1-trichlorosilyl(3-cyanatophenyl)propane, 1,1-trimethoxysilyl(3-cyanatophenyl)propane, 2-(4-cyanatophenyl)ethyltrimethoxysilane, 2-(4-cyanatophenyl)ethyltriethoxysilane, 2-(4-cyanatophenyl)ethyltrichlorosilane, 2-(2-cyanatophenyl)ethyltrimethoxysilane, 2-(2-cyanatophenyl)ethyltriethoxysilane, 2-(2-cyanatophenyl)ethyltrichlorosilane, 2-(3-cyanatophenyl)ethyltriethoxysilane, 2-(3-cyanatophenyl)ethyltrichlorosilane, 2-(3-cyanatophenyl)ethyltrimethoxysilane, 1-(4-cyanatophenyl)ethyltrimethoxysilane, 1-(4-cyanatophenyl)ethyltriethoxysilane, 1-(4-cyanatophenyl)ethyltrichlorosilane, 1-(2-cyanatophenyl)ethyltrimethoxysilane, 1-(2-cyanatophenyl)ethyltriethoxysilane, 1-(2-cyanatophenyl)ethyltrichlorosilane, 1-(3-cyanatophenyl)ethyltriethoxysilane, 1-(3-cyanatophenyl)ethyltrichlorosilane, 1-(3-cyanatophenyl)ethyltrimethoxysilane, 4-(3-trimethoxysilylpropyl)-2-methoxyphenylcyanate, 4-(2-trimethoxysilyipropyl)-2-methoxyphenylcyanate, 4-(1-trimethoxysilylpropyl)-2-methoxyphenylcyanate, 4-(3-triethoxysilylpropyl)-2-methoxyphenylcyanate, 4-(2-triethoxysilylpropyl)-2-methoxyphenylcyanate, 4-(1-triethoxysilylpropyl)-2-methoxyphenylcyanate, 4-(3-trichlorosilylpropyl)-2-methoxyphenylcyanate, 4-(2-trichlorosilylpropyl)-2-methoxyphenylcyanate, 4-(1-trichlorosilylpropyl)-2-methoxyphenylcyanate, 4-(3-trimethoxysilylpropyl)-2,6-bis(methoxy)phenylcyanate, 4-(2-trimethoxysilylpropyl)-2,6-bis(methoxy)phenylcyanate, 4-(3-triethoxysilylpropyl)-2,6-bis(methoxy)phenylcyanate, 4-(2-triethoxysilylpropyl)-2,6-bis(methoxy)phenylcyanate, 4-(3-trichlorosilylpropyl)-2,6-bis(methoxy)phenylcyanate, 4-(2-trichlorosilylpropyl)-2,6-bis(methoxy)phenylcyanate, 4-(2-trimethoxysilylpropyl)-2-ethoxyphenylcyanate, 4-(1-trimethoxysilylpropyl)-2-ethoxyphenylcyanate, 4-(2-triethoxysilylpropyl)-2-ethoxyphenylcyanate, 4-(1-triethoxysilylpropyl)-2-ethoxyphenylcyanate, 4-(2-trichlorosilylpropyl)-2-ethoxyphenylcyanate, 4-(1-trichlorosilylpropyl)-2-ethoxyphenylcyanate, 2,2-[4-(3-trimethoxysilylpropoxyphenyl)](4'-cyanatophenyl)propane, 2,2-[4-(2-trimethoxysilylpropoxyphenyl)](4'-cyanatophenyl)propane, 2,2-[4-(3-triethoxysilylpropoxyphenyl)](4'-cyanatophenyl)propane, 2,2-[4-(2-triethoxysilylpropoxyphenyl)](4'-cyanatophenyl)propane, 2,2-[4-(3-trichlorosilylpropoxyphenyl)](4'-cyanatophenyl)propane, 2,2-[4-(2-trichlorosilylpropoxyphenyl)](4'-cyanatophenyl)propane, 4'-(3-trimethoxysilylpropoxy)-4-biphenylcyanate, 4'-(3-triethoxysilylpropoxy)-4-biphenylcyanate, 4'-(3-trichlorosilylpropoxy)-4-biphenylcyanate, 4'-(2-trimethoxysilylpropoxy)-4-biphenylcyanate, 4'-(2-triethoxysilylpropoxy)-4-biphenylcyanate, 4'-(2-trichlorosilylpropoxy)-4-biphenylcyanate, 4-cyanatophenyl-4'-(3-trimethoxysilylpropoxyphenyl)sulfone, 4-cyanatophenyl-4'-(3-triethoxysilylpropoxyphenyl)sulfone, 4-cyanatophenyl-4'-(3-trichlorosilylpropoxyphenyl)sulfone, 4-cyanatophenyl-4'-(2-trimethoxysilylpropoxyphenyl)sulfone, 4-cyanatophenyl-4'-(2-triethoxysilylpropoxyphenyl)sulfone, and 4-cyanatophenyl-4'-(2-trichlorosilylpropoxyphenyl)sulfone.

The coupling agents of this invention can be used in conjunction with cyanate ester resins to improve the adhesion of the cured resin to substrates. In one embodiment, the coupling agent may be incorporated into the cyanate ester formulation as an additive which improves adhesion to isubstrates upon curing of the cyanate ester formulation. Alternatively, the coupling agent may be used to treat the surface of the substrate as, for example, a primer. The cyanate ester formulation may then be coated onto the primed substrate and cured to give a coating with improved adhesion.

Polyfunctional cyanate ester resins that are useful in the practice of the present invention preferably have the general formula

where p can be an integer from 2 to 7, and wherein Q can comprise a di-, tri-, or tetravalent aromatic hydrocarbon containing from 5 to 30 carbon atoms and zero to 5 aliphatic, cyclic aliphatic, or polycyclic aliphatic, mono- or divalent hydrocarbon linking groups containing 7 to 20 carbon atoms. Optionally, Q may further comprise 1 to 10 heteroatoms selected from the group consisting of non-peroxidic oxygen, sulfur, non-phosphino phosphorus, non-amino nitrogen, halogen, and silicon. The cyanate ester resins may be in the form of monomers, such as 2,2-bis(4-cyanatophenyl)propane which is commercially available as AroCy™ B-10 from Ciba Matrix Resins, Hawthorne, N.J., or cyanate oligomers. Partially cyclotrimerized oligomers, such as AroCy™ B-30 or B-50 (Ciba) where approximately 30 and 50% of the cyanate ester groups of AroCy™ B-10 have been cyclotrimerized can be used. Cyanated novolac resins such as Primaset™ PT-30, PT-60, and PT-90, all commercially available from Allied-Signal Inc., Morristown, N.J., are also useful in the practice of the present invention. Polyaromatic cyanate ester resins containing polycyclic aliphatic diradicals such as Quatrex™ 7187 (Dow Chemical, Midland, Mich.) are also useful in the practice of the present invention. Other commercially available cyanate ester resins include AroCy™ M-10, M-20, M-30, M-50, L-10, XU-366, XU-371, and XU-378, all available from Ciba Matrix Resins and SkyleX™ resins available from Mitsubishi Gas Chemical Co., Inc., Tokyo. Examples of cyanate ester monomers include: 1,3- and 1,4-dicyanatobenzene, 2-tert-butyl-1,4-dicyanatobenzene, 2,4-dimethyl-1,3-dicyanatobenzene, 2,5-di-tert-butyl-1,4-dicyanatobenzene, tetramethyl-1,4-dicyanatobenzene, 4-chloro-1,3-dicyanatobenzene, 1,3,5-tricyanatobenzene, 2,2'- or 4,4'-dicyanatobiphenyl, 3,3',5,5'-tetramethyl-4,4'- dicyanatodiphenyl, 1,3-, 1,4-, 1,5-, 1,6-, 1,8-, 2,6-, or 2,7-dicyanatonaphthalene, 1,3,6-tricyanatonaphthalene, bis(4-cyanatophenyl)methane, bis(3,5-dimethyl-4-cyanatophenyl) methane (AroCy™ M-10), 2,2-bis(4-cyanato-phenyl) propane (AroCy™ B-10), 1,1,1-tris(4-cyanatophenyl) ethane, 1,1-bis(4-cyanatophenyl)ethane (AroCy™ L-10), 2,2-bis(3,5-dichloro-4-cyanatophenyl)propane, 2,2-bis(3,5-dibromo-4-cyanatophenyl)propane, bis(4-cyanatophenyl) ether, 4,4'-(1,3-phenylenediisopropylidene)diphenylcyanate (AroCy™ XU-366), bis(4-cyanato-phenyl)ketone, bis(4-cyanatophenyl)thioether, bis(4-cyanatophenyl)sulfone, tris (4-cyanatophenyl)phosphite, and tris(4-cyanatophenyl) phosphate. Essentially any di-or polyfunctional phenolic compound which reacts with cyanogen halide in the presence of a base to form a di- or polyfunctional aromatic cyanate ester compound may be useful in the present invention.

Monofunctional cyanate ester compounds such as phenylcyanate, 4-cumylphenylcyanate, 4-t-butylphenylcyanate, and 4-phenylphenylcyanate may also be incorporated into the cyanate ester formulations. The use of monofunctional cyanate esters in combination with polyfunctional cyanate ester resins can lower crosslink density in the cured resin and provide cured compositions with enhanced flexibility.

Curing agents useful in the practice of the present invention may be chosen from those known in the art. Representative useful curing agents include strong Lewis acids such as $AlCl_3$ and $BF_3$, protonic acids such as HCl and $H_3PO_4$, amines such as triethylamine and 1,4-diazabicyclo[2.2.2] octane, metal salts of carboxylic acids such as tin octoate and zinc naphthenate, and various other materials such as sodium hydroxide, phosphines, phenols, imidazoles, metal acetylacetonates, organic peroxides, carboxylic acid anhydrides, organic azo compounds. Organometallic compounds, that is compounds containing at least one transition metal atom to carbon atom covalent bond, are also useful curing agents for cyanate ester resins and are described in U.S. Pat. No. 5,215,860. Curing is accomplished in the presence of energy, generally heat optionally in the presence of light, preferably at a temperature in the range 60 to 300° C., more preferably 100 to 200° C.

A composition of matter of the present invention preferably comprises an aromatic cyanate ester silane comprising at least one cyanate ester group and at least one alkoxysilyl group. The composition optionally further comprises a cyanate ester resin. In the presence of a substrate the aromatic cyanate ester silane functions as a coupling agent for the cyanate ester resin. The curable compositions are useful as composite, adhesive and coating compositions. Typically the solvent-free compositions have a cure time less than 300 seconds at a temperature of 180° C. when the amount of the cyanate ester curing agent, as disclosed above, is in the range of from 0.1 to 5% by weight. The amount of coupling agent can be in the range of more than 0 and up to 15 parts coupling agent to 100 parts cyanate ester resin, preferably 1 to 5 parts coupling agent per hundred parts resin.

Substrates suitable in the practice of this invention which can be inorganic or organic substrates may take essentially any physical shape. They may, for example, be substantially flat surfaces such as glass plate, fine powders such as graphite or fumed silica fillers, fibers such as glass reinforcing fibers, or large particles such as glass bubbles or beads. Substrates suitable in the practice of this invention may be of essentially any chemical composition provided that the surface of the substrate has groups, preferably hydroxyl groups, which are capable of reacting with the hydrolyzable groups of the coupling agent thereby attaching the Si group to the substrate surface. Illustrative examples of substrates suitable in the practice of this invention include glasses such as soda lime glass, borosilicate glass, and glass coated with electrically conductive indium-tin oxide layers; metals or metalloids with oxide layers such as cadmium, silicon, zinc, aluminum, iron, copper, nickel, tin, brass, steel, and titanium; and ceramics such as alumina, magnesia, silica, and magnesium silicate.

The cyanate ester formulations of the present invention (coupling agent plus resin and optional adjuvants) can be coated onto, into, or intimately mixed with a substrate to provide coated composites or filled molded articles to provide coated filled articles.

The cyanate ester formulations may be in the form of monolithic structures, moldable liquids or solids, dry film adhesives, pressure sensitive adhesives, dispensable liquids, or solvent-borne coatings.

In a preferred embodiment, an adhesive film comprises
(a) 75 to 100 percent by volume of an adhesive component comprising:
(1) 5 to 75 percent by weight of a thermoplastic polymer,
(2) 95 to 25 percent by weight of a cyanate ester resin,
(3) 0.1 to 5 percent by weight of an aromatic cyanate ester silane coupling agent of the present invention, the coupling agent comprising at least one hydrolyzable silyl group, and
(4) 0.1 to 5 percent by weight of a catalyst for curing a cyanate ester resin; and
(b) 0 to 25 percent by volume of electrically conductive particles.

Preferably, the film has a cure time of less than 300 seconds at a temperature of 180° C. When conductive particles are present, preferably in the range of 1 to 25 percent by volume, more preferably in the range of 2 to 10 percent by volume, the adhesive film is antisotropically conductive adhesive film.

Compositions of the present invention are particularly useful as electronic adhesives. Electronic adhesives are used to simultaneously adhesively bond and electrically interconnect two circuit bearing substrates. They may be in the form of liquid adhesives which may be dispensed by any of a number of means, such as screen printing or by syringe, or they may be film adhesives which may be free standing or placed on a discardable carrier film. Depending upon the nature of the circuitry to be bonded, the electronic adhesives may or may not have particles of an electrically conductive material dispersed therein. For example, electrical contact may be made by metallic features on the substrates, such as metallic projections on a "bumped" chip, which protrude through the adhesive during the bonding step. Alternatively, a film adhesive can be loaded with electrically conductive particles such that no electrical conductivity is possible in the plane of the film but electrical conductivity is provided through the thickness of the film. Such films are typically referred to as "z-axis adhesive films" ("ZAF") or "anistropically conductive adhesive films" ("ACF"). These film adhesives have the ability to establish multiple discrete electrical connections, often in extremely close proximity, between two microelectronic components. Cyanate ester resin containing ZAF materials may be made by a variety of methods including solvent casting as described in U.S. Pat. Nos. 5,143,785 and 5,330,684, and solventless free radical polymerization as described in the co-pending application U.S. Ser. No. 08/078,981. In any case, adhesion of the cyanate ester containing ZAF to substrates, such as ITO (indium-tin oxide) coated glass, may be improved by incorporation of the aromatic cyanate ester silane coupling agent as described herein.

In a ZAF material, conductive particles provide multiple discrete interconnections for each circuit trace or pad. The conductive particles desirably can be in a size and loading in accordance with the end use application. Factors, such as the width of circuit traces or pads and distances between adjacent circuit traces or pads can be used to determine the particle size and volume density. The conductive particles desirably can be sufficiently small so as not to span the distance between adjacent circuit traces or pads so as to prohibit adjacent traces or pads from shorting out; and can be present in sufficient numbers so as to provide multiple discrete contact points at each trace or pad location. Typically, the particle size diameters range from 3 to 30 micrometers ($\mu$m), and preferably 4–15 $\mu$m. Useful conductive particle loadings can be in the range of more than zero to 25% by volume compared to the adhesive, preferably 0.2–25% by volume, and most preferably 1–10% by volume. For example, a particle population having diameters of 10–15 $\mu$m and loaded at approximately 1–10% by weight into the adhesive composition can provide interconnections for trace sizes as small as 100,000 $\mu m^2$ and positioned with as little as 50 $\mu$m separation between adjacent traces. Any of several particle types can be selected based on the end use application. Factors such as metallurgy and the hardness of the substrate can be used to select the particle type for a given application. Useful conductive particles for ZAF materials include metal particles, metallized polymer particles, metallized glass particles, and carbon particles.

Thermoplastics, such as polyvinyl acetal, polysulfones, polyesters, polyamides, polycarbonates, polyethers, and phenoxy resins, are desirable in solvent cast cyanate ester containing adhesive films and ZAF materials as they enhance the film handling characteristics of the resulting material. The thermoplastic can be present at about 5 to 75% by weight, and for a free-standing or transfer adhesive is preferably present at about 20 to 60% by weight. In use, substantially solvent-free ZAF material is interposed between the substrates to be connected, circuit traces or pads are aligned, and heat and pressure are applied to cure the ZAF and provide an adhesively bonded and electrically connected structure. Typically, the adhesive bond forms in less than 300 seconds at temperatures of 180° C. and pressure of 1.5 megapascals.

Adjuvants such as solvents, thermoplastics, pigments, electrically and/or thermally conductive particles, abrasive particles, stabilizers, antioxidants, inert fillers, binders, plasticizers, fungicides, bactericides, surfactants, blowing agents, and other additives as is known to those skilled in the art can be added to the compositions of this invention in amounts suitable for their intended purposes.

The cyanate ester formulations may have utility as, for example, insulating electronic adhesives, electrically conductive electronic adhesives, thermally conductive adhesives, structural adhesives, conformal coatings, protective coatings, decorative coatings, binders, and reinforced structural composites.

Objects and advantages of this invention are further illustrated by the following examples, but the particular materials and amounts thereof recited in these examples, as well as other conditions and details, should not be construed to unduly limit this invention.

EXAMPLES

Example 1

Synthesis of 4-(2-propenyl)phenol.

To 50.01 g (337.4 mmol) of 1-methoxy-4-(2-propenyl) benzene (Aldrich Chemical Company, Milwaukee, Wis.) dissolved in 300 mL of anhydrous methylene chloride was added dropwise 375 mL (375 mmol) of 1.0 M boron tribromide (Aldrich) in methylene chloride. The reaction was run under nitrogen at room temperature and the mixture was stirred for 1 hour. The mixture was poured over 1000 mL of crushed ice, stirred for 5 minutes, and transferred to a separatory funnel. The organic layer was drained and saved. The boron salts were transferred to a filter containing Celite™ (Aldrich Chemical Co., Milwaukee, Wis.) and the filter containing the salts was washed with portions of methylene chloride and then water. The filtrate was transferred to a separatory funnel and the organic and aqueous layers were separated. The aqueous layer was extracted with four 100mL portions of methylene chloride. The methylene chloride solutions were pooled, dried over anhydrous magnesium sulfate, and filtered. The solvent was removed under vacuum to yield 25.27 g (56%) of crude 4-(2-propenyl) phenol. The crude product was distilled twice at reduced pressure to yield 20.34 g (45%) of 4-(2-propenyl)phenol. The NMR data was consistent with that reported by Rajashekhar and coworkers (*J. Biol. Chem.* 1984, 259, 6925).

Example 2

Synthesis of 3-(4-cyanatophenyl)propyltrimethoxysilane by Method A.

To a solution of 2.142 g (15.96 mmol) of 4-(2-propenyl) phenol (prepared as in Example 1) in 15 mL of methylene chloride was added 2.351 g (22.19 mmol) of cyanogen bromide (Aldrich). The mixture was cooled in an ice-salt bath and 3 mL (22 mmol) of triethylamine was added dropwise with stirring. The mixture was stirred for an additional 15 minutes. The solvent was removed under vacuum and the mixture was transferred to a separatory funnel with 25 mL of water and 75 mL of petroleum ether (30–60° C. boiling range). The aqueous and organic layers were separated. The organic layer was washed with three 50 mL portions 6 N hydrochloric and one 50 mL portion of saturated sodium bicarbonate, dried over anhydrous magnesium sulfate, and filtered. The solvent was removed under vacuum to yield 1.668 g (66%) of crude 1-cyanato-4-(2-propenyl)benzene. The product was distilled to yield 1.307 g (51%) of 1-cyanato-4-(2-propenyl)benzene. The structure of the product was verified by IR and NMR spectroscopy. The product can be further purified by passing the product through a silica gel column using 1% toluene in petroleum ether as the solvent system.

To 3.94 g (24.75 mmol) of purified 1-cyanato-4-(2-propenyl)benzene, prepared as described above, at 65° C. was added 10 $\mu$L of a 3% solution of Karstedt's™ catalyst (platinum-divinyltetramethyldisiloxane complex) in xylene (United Chemical Technologies, Bristol, Penn.). Trimethoxysilane (Aldrich) was added in 500 $\mu$L increments followed by 10 $\mu$L increments of the catalyst solution until NMR showed that the reaction was more than 80% complete. The product was distilled twice to yield 2.94 g (42%) of 3-(4-cyanatophenyl)propyltrimethoxysilane. The structure of the product was verified by IR and NMR.

Example 3

(a) Synthesis of 3-(4-cyanatophenyl) propyltrimethoxysilane) by Method B.

To a 100 mL 3-necked round-bottomed flask with a magnetic stirrer and thermometer, open to the atmosphere, was added 9.8 grams 4-allyl phenol and 10.23 mL trimethoxysilane. To this was added 0.03 mL Karstedt's catalyst (as defined in Example 2). The reaction slowly exothermed to 30° C. over a four-minute period. After seven minutes the temperature dropped to 29° C. and 0.03 mL Karstedt's catalyst was added. The mixture exothermed to 32° C. in four minutes. After 40 minutes the temperature dropped to 29° C. and 0.03 mL Karstedt's catalyst was added. The mixture exothermed to 32° C. and after stirring 35 minutes 0.03 mL Karstedt's catalyst was added. The mixture was stirred two hours and 15 minutes and 0.03 mL catalyst was added. The mixture was stirred 2 hours. $^1$H-NMR showed no residual starting material. The mixture was transferred to a 500 mL 3-necked round-bottomed flask with thermometer and addition funnel. The product was diluted with 150 mL dichloromethane and 25 g cyanogen bromide was added. The mixture was cooled to 7° C. in an ice bath. To this was added 21.38 mL triethylamine dropwise at a rate such that the temperature did not go above 10° C. The mixture was stirred for two hours. The reaction was filtered through Celite™ and diluted with 200 mL dichloromethane. The mixture was extracted two times with water. The organic phase was dried over magnesium sulfate, filtered, and the solvent was removed in vacuo. The product was kept overnight in the freezer. The mixture was purified by distillation at reduced pressure to give 2.8 grams of pure 3-(4-cyanatophenyl)propyltrimethoxysilane. The structure of the product was confirmed spectroscopically.

(b) Synthesis of 3-(2-cyanatophenyl)propyltrimethoxysilane.

To a 50 mL 3-necked round bottom flask with thermometer, open to the atmosphere, was added 2.0 grams 2-allyl phenol and 1.90 grams trimethoxysilane. To this was added 0.03 mL Karsteds catalyst (as defined in Example 2). The reaction was exothermic and an ice bath was applied once the temperature rose above 27° C. The temperature reached 45° C. and then dropped to 21° C. The temperature was held at 21° C. with no external cooling for 10 minutes. An additional 0.2 mL (0.1 equivalents) trimethoxysilane was added and 0.005 mL Karsteds catalyst. The reaction was slightly exothermic and bubbled. After a total reaction time of 2 hours and 45 minutes proton NMR showed the desired product to be present with no remaining starting material. The reaction was diluted with 30 mL dichloromethane and 5.0 grams cyanogen bromide was added. The mixture was cooled in an ice bath to 5° C. Triethylamine (4.36 mL) was added dropwise at such a rate that the temperature remained at 10° C. The total addition time was 15 minutes. The mixture was then stirred an additional 10 minutes at 5° C. and the cooling bath was removed. The resulting mixture was stirred at room temperature for one hour and 15 minutes. The mixture was diluted with 50 mL dichloromethane and extracted two times with 50 mL portions of water. The organic phase was dried over magnesium sulfate, filtered, and the solvent was removed in vacuo. The product was distilled using an aspirator vacuum of 15 mm Hg to remove the triethyl amine. The product was distilled at reduced pressure to give a fraction that contained approximately 50% of 3-(2-cyanatophenyl)propyltrimethoxy silane. The structure of the product was confirmed spectroscopically.

Example 4

Plain glass microscope slides were utilized to test the silane coupling agent. Three slides (comparative) were dipped in a 1% solution of 3-glycidoxypropyltrimethoxysilane in ethanol; three slides were dipped in a 1% solution of 3-(4-cyanatophenyl)propyltrimethoxysilane (from Example 3) in ethanol; and three slides (comparative) were left untreated. The treated slides were allowed to dry. The cyanate ester AroCy B-30 was heated in an oven to 65° C. until it flowed easily and 0.25% by weight cyclopentadienyl iron dicarbonyl dimer catalyst was added and thoroughly mixed. Approximately 0.3 g of the catalyzed AroCy B-30 mixture was placed on each of the nine slides described above and these were placed in a 180° C. oven for ten minutes. Upon cooling, the slides were placed in a water bath which was maintained at 65° C. and stirred slowly to ensure circulation of the water. The bath was monitored periodically and the slides were removed and evaluated. Evaluation consisted of applying light to moderate pressure with the tip of a scalpel blade at the edge of the adhesive-glass interface. Failure was indicated by the clean removal of the adhesive from the glass. Slides that did not fail were returned to the bath. It was observed that the blank or untreated slides failed within 1 hour. The slides treated with 3-glycidoxypropyltrimethoxysilane failed when tested after 20 hours. The slides treated with 3-(4-cyanatophenyl)propyltrimethoxysilane failed after 192 hours.

Example 5

Two formulations were prepared using the proportions in Table 1. The cyanate ester and the polyvinylacetal were dissolved in methyl ethyl ketone, followed by addition of the cyanate silane coupling agent, the manganese acetylacetonate catalyst which was dissolved in methyl ethyl ketone, and the gold-plated conductive particles, all being added and mixed into the solution. The dispersion was stirred until uniform. A comparative sample was prepared with an epoxy silane coupling agent in place of the cyanate silane. These dispersions were coated onto a silicone-treated PET film using a knife coater and dried for 10 minutes at 40° C. The thickness of the adhesives was about 25 microns.

TABLE 1

| | Parts (by weight) | |
|---|---|---|
| Component | Example 5 | Comparative Example 5 |
| Cyanate ester[1] | 60 | 60 |
| Polyvinylacetal[2] | 40 | 40 |
| Cyanate silane coupling agent[3] | 2 | 0 |
| Epoxy silane coupling agent[4] (comparative) | 0 | 2 |
| Manganese acetylacetonate[5] | 1 | 1 |
| Au/Ni/benzoguanamine-resin conductive particles[6] | 12.5 | 12.5 |
| Methyl ethyl ketone | 170 | 170 |

[1]BT2160RX ™ from Mitsubishi Gas Chemical Co., Inc.
[2]S-Lec KS-1 ™ from Sekisui Chemical Co., Ltd.
[3]3-(4-cyanatophenyl)propyltrimethoxysilane
[4]3-glycidoxypropyltrimethoxysilane
[5]$C_{15}H_{21}O_6Mn$ from Dojindo Laboratories
[6]20GNR4.6-EH ™ from Nippon Chemical Industrial Co., Ltd.

The adhesive film was peeled off the liner and placed onto the glass substrate on a bonding stage. A 3M 120 test chip was attached to the thermode of the bonder. The chip was then applied to the glass substrate with bonding accomplished by use of a pulse heat bonder with a bond time of 2 minutes at 180° C. under 15 kg/cm$^2$ (1.5 MPa) of pressure. The thermode setpoint was 203° C. When the bonding was finished and the pressure was released, the thermode still maintained the bonding temperature similar to a steady heater. The details of the glass substrate and the chip are described in Table 2.

TABLE 2

| Glass Substrate | 3M Test Chip |
|---|---|
| Material: SiO$_2$-coated glass with ITO (indium-tin oxide) Size: 39 × 39 × 1.1 mm Pitch: 200 micrometer Width of ITO conductor: 100 micrometer Sheet resistance: 30 ohm/square | Material: silicon with SiO$_2$ passivation Size: 6.8 × 6.8 × 0.5 mm Au bump pitch; 200 micrometer Size of bump: 100 × 100 × 25 micrometer each |

Interconnection resistances were measured using a four-wire method commonly used in the art with 0.1 mA DC. In this method, two interconnections and one aluminum daisy chain (uninterruped claim) resistance were included in the measured value. The data is shown in TABLE 3, below.

TABLE 3

| Adhesive Film | Aging Time (hrs) | Max (ohm) | Ave (ohm) | Min (ohm) |
|---|---|---|---|---|
| Example | 0 | 4.0 | 2.2 | 1.1 |
| Example | 24 | 4.9 | 2.8 | 1.3 |
| Example | 168 | 12.9 | 4.6 | 1.7 |
| Example | 500 | 19.4 | 6.8 | 2.6 |
| Example | 1000 | 36.8 | 9.7 | 3.7 |
| Comparative | 0 | 4.7 | 2.4 | 1.0 |
| Comparative | 24 | 6.7 | 3.2 | 1.1 |
| Comparative | 168 | 13.5 | 4.7 | 1.1 |
| Comparative | 500 | 21.6 | 7.1 | 2.3 |
| Comparative | 1000 | 83.5 | 15.5 | 3.4 |

The data of TABLE 3 show interconnection resistances after 1000 hours aging at 80° C. and 95% relative humidity.

Figure 2:
FIG. 2 is a micrograph (9.5× enlarged) showing a 3M test chip bonded, using a comparative composition, to an indium-tin oxide glass substrate.

The appearance of the bonds was observed using a microscope with polarized light. The photomicrographs of FIGS. 1 and 2 show the appearance of the bonds after 1000 hours aging at 80° C. and 95% relative humidity. In both of the FIGS., dendritic structures can be seen. These structures are artifacts of the bonding procedure which do not significantly affect the strength of the bond. The comparative sample depicted in FIG. 2 show that delamination occurred over almost the whole surface of the chip. This was evidenced by the cloudy or mottled appearance which partially obscured the insignia "3M 120" on the chip. Further, the interconnection resistance had increased considerably over 1000 hours as shown by the resistance data of TABLE 3. In contrast, the present invention sample, depicted in FIG. 1, showed significant delamination did not occur. Also, the interconnection resistance was superior to that of the comparative sample even after 1000 hours. This showed that the coupling agent of the present invention improved the stability of the bond under humid conditions compared to the comparative coupling agent.

Various modifications and alterations of this invention will become apparent to those skilled in the art without departing from the scope and spirit of this invention, and it should be understood that this invention is not to be unduly limited to the illustrative embodiments set forth herein.

We claim:

1. A composition of matter comprising an aronmatic cyanate ester silane comprising at least one cyanate ester group and at least one hydrolyzable silyl group further comprising a polyfunctional cyanate ester resin.

2. The composition of matter according to claim 1 wherein said cyanate ester resin has the formula $$Q(OCN)_p$$

wherein p is an integer in the range of 2 to 7, and Q comprises a di-, tri-, or tetravalent aromatic hydrocarbon containing from 5 to 30 carbon atoms and zero to 5 aliphatic, cyclic aliphatic, or polycyclic aliphatic, mono- or divalent hydrocarbon linking groups comprising 7 to 20 carbon atoms.

3. The composition according to claim 2 wherein Q further comprises 1 to 10 heteroatoms selected from the group consisting of non-peroxidic oxygen, sulfur, non-phosphino phosphorus, non-amino nitrogen, halogen, and silicon.

4. The composition according to claim 2 wherein said cyanate ester resin is at least one of a monomer and an oligomer.

5. The composition according to claim 1 further comprising a monofunctional cyanate ester.

6. The composition according to claim 1 further comprising electrically conductive material.

7. The composition according to claim 1 further comprising a curing agent for said cyanate ester resin.

8. A method comprising the steps:

reacting an aromatic hydroxyl compound which contains at least one aliphatic or cycloaliphatic carbon-to-carbon double bond with
i) cyanogen halide and a base, and
ii) a silane containing both an Si—H group and a hydrolyzable group, materials of steps i) and ii) being reacted in either order, to provide a cyanate ester silane compound;

further comprising the step of admixing a polyfunctional cyanate ester resin with the resulting cyanate ester silane compound.

9. The method according to claim 8 further comprising the step of admixing a curing agent for said cyanate ester resin into said composition.

10. The method according to claim 9 further comprising the step of coating said composition on a substrate.

11. The method according to claim 10 further comprising the step of adding energy to cure said coating on said substrate.

12. A method of coupling a cyanate ester resin to a substrate comprises the steps of a) admixing said cyanate ester resin with a cyanate ester resin coupling agent having the formula $$\{(NCO)_c-Ar-U'-\}_a SiR_b Z_{\{4-(a+b)\}}$$

where Ar is as described above, NCO is a cyanate group directly bound to an aromatic ring of Ar, c=an integer 1 to 5, U' is an organic group resulting from the hydrosilation of the group U defined above, a=an integer 1 to 3, most preferably 1, R is as defined above, b=0 or 1 or 2, with the proviso that a+b is less than or equal to 3, and Z is as described above;

b) coating said admixture onto or into a substrate to form a composite structure, and c) adding energy to cure said composite structure.

13. An adhesive film comprising (a) 75 to 100 percent by volume of an adhesive component comprising:

(1) 5 to 75 percent by weight of a thermoplastic polymer,
(2) 95 to 25 percent by weight of a cyanate ester resin,
(3) 0.1 to 5 percent by weight of an aromatic cyanate ester silane according to claim 1, and
(4) 0.1 to 5 percent by weight of a catalyst for curing said cyanate ester resin; and (b) 0 to 25 percent by volume of electrically conductive particles.

14. The adhesive film according to claim 13, wherein said thermoplastic polymer is selected from the group consisting of polyvinyl acetals, polysulfones, polyesters, polyamides, polycarbonates, polyethers, and phenoxy resins.

15. The adhesive film according to claim 13, wherein said aromatic cyanate ester silane is 3-(4-cyanatophenyl)propyl trimethoxysilane.

16. The adhesive film according to claim 13, wherein said electrically conductive particles are present in the range of more than zero to 25 percent by volume.

17. The adhesive film according to claim 16 which is an anisotropically conductive adhesive film.

* * * * *

UNITED STATES PATENT AND TRADEMARK OFFICE
CERTIFICATE OF CORRECTION

PATENT NO.    : 6,217,943 B1
DATED         : April 17, 2001
INVENTOR(S)   : Hall, Joyce B.

It is certified that error appears in the above-identified patent and that said Letters Patent is hereby corrected as shown below:

Title page,
Item [62], Related U.S. Application Data, "Jun. 5, 1996" should read
-- Jun. 5, 1995 --.

Column 1,
Line 47, "acryloyl" should read -- acrylyl --.

Column 2,
Line 47, "an" should read -- a --.

Column 5,
Line 55,

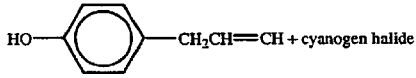

should read --
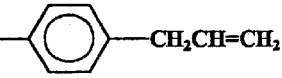
--

Column 7,
Line 43, "trimethoxysilyipropyl" should read -- trimethoxysilylpropyl --.

Column 8,
Line 24, "isubstrates" should read -- substrates --.
Line 60, "SkyleX[TM]" should read -- Skylex[TM] --.

UNITED STATES PATENT AND TRADEMARK OFFICE
CERTIFICATE OF CORRECTION

PATENT NO. : 6,217,943 B1
DATED : April 17, 2001
INVENTOR(S) : Hall, Joyce B.

It is certified that error appears in the above-identified patent and that said Letters Patent is hereby corrected as shown below:

Column 12,
Line 62, "Example 3" should read -- Example 3.(a) --.
Line 63, delete "(a)".

Signed and Sealed this

Twentieth Day of May, 2003

JAMES E. ROGAN
*Director of the United States Patent and Trademark Office*